(12) United States Patent
Kay

(10) Patent No.: US 8,672,843 B2
(45) Date of Patent: Mar. 18, 2014

(54) AUTOMATED PROTOCOL FOR DETERMINING PSYCHIATRIC DISABILITY

(75) Inventor: Lay Kay, Pasadena, CA (US)

(73) Assignee: QTC Management, Inc., Diamond Bar, CA (US)

( * ) Notice: Subject to any disclaimer, the term of this patent is extended or adjusted under 35 U.S.C. 154(b) by 1190 days.

(21) Appl. No.: 11/604,358

(22) Filed: Nov. 27, 2006

(65) Prior Publication Data

US 2008/0124688 A1 May 29, 2008

(51) Int. Cl.
*A61B 5/00* (2006.01)
*G06F 19/00* (2011.01)

(52) U.S. Cl.
CPC .................................. *G06F 19/30* (2013.01)
USPC .......................................... 600/301; 434/236

(58) Field of Classification Search
USPC .................... 600/300–301; 434/236
See application file for complete search history.

(56) References Cited

U.S. PATENT DOCUMENTS

| | | | | |
|---|---|---|---|---|
| 5,377,258 | A | * | 12/1994 | Bro ........................... 379/106.02 |
| 5,435,324 | A | * | 7/1995 | Brill .............................. 128/897 |
| 5,692,501 | A | * | 12/1997 | Minturn ........................ 600/301 |
| 5,722,418 | A | * | 3/1998 | Bro ............................... 600/545 |
| 5,879,163 | A | * | 3/1999 | Brown et al. ................. 434/236 |
| 5,897,493 | A | * | 4/1999 | Brown .......................... 600/300 |
| 5,961,332 | A | * | 10/1999 | Joao ............................. 434/236 |
| 6,108,665 | A | | 8/2000 | Bair et al. |
| 6,263,330 | B1 | | 7/2001 | Bessette |
| 6,425,764 | B1 | * | 7/2002 | Lamson ........................ 434/236 |
| 6,581,038 | B1 | | 6/2003 | Mahran |
| 6,607,484 | B2 | * | 8/2003 | Suzuki et al. ................. 600/300 |
| 2002/0046346 | A1 | | 4/2002 | Evans |
| 2003/0037063 | A1 | * | 2/2003 | Schwartz ................... 707/104.1 |
| 2004/0122704 | A1 | | 6/2004 | Sabol et al. |
| 2004/0122705 | A1 | | 6/2004 | Sabol et al. |
| 2004/0122707 | A1 | | 6/2004 | Sabol et al. |
| 2004/0122708 | A1 | | 6/2004 | Avanish et al. |
| 2004/0141661 | A1 | | 7/2004 | Hanna et al. |
| 2005/0261957 | A1 | * | 11/2005 | Fisher et al. .................... 705/11 |
| 2009/0182578 | A1 | * | 7/2009 | Ozersky ........................... 705/3 |

* cited by examiner

*Primary Examiner* — Bill Thomson
*Assistant Examiner* — Bobby Soriano
(74) *Attorney, Agent, or Firm* — James W. Hill; Nathan S. Smith; McDermott Will & Emery LLP

(57) ABSTRACT

A system for determining a psychiatric status of a person is described, the system including an activity module that outputs first data indicative of the person's activities of daily living, a social module that outputs second data indicative of the person's social functioning in a work-like setting, a persistence module that outputs third data indicative of the person's concentration persistence, a stress module that outputs fourth data indicative of the person's ability to tolerate stress, and a processing module that outputs fifth data indicative of a psychiatric disability determination based on outputs from said activity module, said social module, said persistence module, and said stress module. In certain embodiments, at least one of the activity module, the social module, the persistence module, and the stress module comprises computer executable instructions. The system may also feature a user interface configured to display the psychiatric disability determination.

23 Claims, 3 Drawing Sheets

---

*Sample Psychiatric Disability Status Determination Report*

301

Patient: Doe, John
Date: 5/12/2006

302

Activities of daily living: 80%
Social functioning in a work-like setting: 35%
Concentration persistence: 20%
Ability to tolerate stress: 55%

303

Overall Psychiatric Disability Status Determination:
35% Competency Entering Employment Market
Should NOT Return to Prior Employment 1. Others are severely critical of my mistakes. True or False?
2. I am happiest when my family praises me. True or False?
3. I doubt my life will improve in the future. True or False?
4. I prefer to be the center of attention at parties. True or False?
. . .

FIG. 3

Sample Psychiatric Disability Status Determination Report

301 — Patient: Doe, John
Date: 5/12/2006

302 —
Activities of daily living: 80%
Social functioning in a work-like setting: 35%
Concentration persistence: 20%
Ability to tolerate stress: 55%

303 —
*Overall Psychiatric Disability Status Determination:*
*35% Competency Entering Employment Market*
*Should NOT Return to Prior Employment*

AUTOMATED PROTOCOL FOR DETERMINING PSYCHIATRIC DISABILITY

BACKGROUND

1. Field of the Invention

The present invention relates to methods and systems for gathering and processing data to support rating decisions in the adjudication of psychiatric disability requests.

2. Description of the Related Art

In the field of disability evaluation there are numerous approaches to assessment of basic or residual functioning. The generally accepted method has been to utilize a large battery of testing instruments to cover all aspects of the individual's functioning that could impact normal life, especially job performance. This testing material is often overlapping, redundant, or unnecessary. Mental health factors such as mood disorders and psychosis which affect the individual's functioning are evaluated independently as part of a diagnostic assessment. For example, the Minnesota Multiphasic Personality Inventory test ("MMPI"), Draw-a-Person test ("DAP"), Rorschach test, and/or other tests as well as an extensive clinical interview may be necessary to classify a diagnosis according to the *Diagnostic and Statistical Manual of Mental Disorders, Fourth Edition* ("DSM-IV"). However, with such instruments, the issue of motivation, adaptive capacities, or specific mental status questions dealing with memory function, cognitive processing, abstraction, and other mental functions are not specifically assessed or quantified in applicable fashion to the question of work ability.

Additionally, job performance assessments similarly do not answer these questions or those of diagnostic issues impacting work performance. Specific mental status instruments concentrate on one or another facet of mental functioning to the exclusion of motivational and adaptive abilities. For example, many frequently used tests of mental status focus primarily on cognitive abilities to exclude the limitations of dementia. Some instruments focus on specific conditions such as aphasia in brain injury as part of a neuropsychological battery to determine degree or type of impairment. They do not, however, focus on determining motivational and adaptive abilities, which are of importance to determining a disability evaluation especially as it relates to the workplace.

SUMMARY

Thus, it would be advantageous to provide a useful and reliable tool for determining the abilities and limitations that individuals have in going about their activities of daily living. Of special interest is how this information translates into functioning in the workplace.

Certain forms of empirical evidence are widely accepted as a necessary part of any evaluation for disability that relates to work type activities. Those abilities found minimally necessary include activities of daily living; social functioning; concentration, persistence, and pace; and ability to tolerate stress in work-like environments.

Another aspect of the disclosure provides for an enhanced mental status examination. One embodiment encompasses and surpasses a standard mental status examination as known in the art. Such prior art mental status examinations have been used to identify specific cognitive disorders such as dementias and traumatic brain injuries, such as the Folstein Mini-Mental Status exam. These standard mental status examinations stop short of accounting for adaptive abilities, personality and social factors affecting motivation, attempts at malingering, assessing cadence and persistence, problem solving and judgment, and sample only a small range of elements needed in a work setting.

In some embodiments, a system is disclosed for determining a psychiatric status of a person. The system comprises an activity module that outputs first data indicative of the person's activities of daily living. The system also comprises a social module that outputs second data indicative of the person's social functioning in a work-like setting. The system also comprises a persistence module that outputs third data indicative of the person's concentration persistence. The system also comprises a stress module that outputs fourth data indicative of the person's ability to tolerate stress. The system also comprises a processing module that outputs fifth data indicative of a psychiatric disability determination based on outputs from said activity module, said social module, said persistence module, and said stress module.

In some embodiments of the system, the first data is derived from at least one of a level of self-care, a level of personal hygiene, communication ability, travel ability, and an amount of public transportation use. In some embodiments of the system, the second data is derived from at least one of a communication capacity, an extent of cooperation with others, a level of acceptance of authority, and a reliance upon peer support. In some embodiments of the system, the third data is derived from at least one of an ability to remember multi-part instructions, a level of persistence at a single task, a level of motivation, a level of self-discipline, and a level of personal independence. In some embodiments, the fourth data is derived from at least one of flexibility, a coping capacity, an ability to adapt, and a degree of personal integration. In some embodiments of the system, at least one of the activity module, the social module, the persistence module, and the stress module comprises computer executable instructions. In some embodiments of the system, the system further comprises a user interface configured to display the psychiatric disability determination.

In some embodiments, a method for determining a psychiatric status of a person is disclosed. The method comprises receiving first data indicative of the person's activities of daily living. The method also comprises receiving second data indicative of the person's social functioning in a work-like setting. The method also comprises receiving third data indicative of the person's concentration persistence. The method also comprises receiving fourth data indicative of the person's ability to tolerate stress. The method also comprises processing the first, second, third and fourth data to generate a psychiatric disability determination. The method also comprises outputting to an output device a data set indicative of the psychiatric disability determination.

In some embodiments of the method, the psychiatric disability determination comprises an employment determination. In some embodiments of the method, receiving the first, second, third and/or fourth data comprises receiving at least a portion of the first, second, third and/or fourth data from a user. In some embodiments of the method, receiving the first, second, third and/or fourth data comprises receiving at least a portion of the first, second, third and/or fourth data from an electronic database. In some embodiments of the method, the receiving the first, second, third and/or fourth data comprises receiving numerical scores in response to one or more tests of the person. In some embodiments of the method, the said receiving the first, second, third and/or fourth data comprises receiving response to one or more queries presented to the person. In some embodiments of the method, the concentration persistence comprises a pace from a first task to a second task.

In some embodiments, a computer executable program for assisting determining a psychiatric status of a person is disclosed. The computer executable program comprises a first module configured to receive first data indicative of the person's activities of daily living. The computer executable program also comprises a second module configured to receive second data indicative of the person's social functioning in a work-like setting. The computer executable program also comprises a third module configured to receive third data indicative of the person's concentration persistence. The computer executable program also comprises a fourth module configured to receive fourth data indicative of the person's ability to tolerate stress. The computer executable program also comprises a fifth module configured to process said first, second, third and fourth data and configured to output a psychiatric disability determination for later publication to an output device.

In some embodiments of the computer executable program, the first data is derived from at least one of: a level of self-care, a level of personal hygiene, communication ability, travel ability, and an amount of public transportation use. In some embodiments of the computer executable program, the second data is derived from at least one of: a communication capacity, an extent of cooperation with others, a level of acceptance of authority, and a reliance upon peer support. In some embodiments of the computer executable program, the third data is derived from at least one of: an ability to remember multi-part instructions, a level of persistence at a single task, a level of motivation, a level of self-discipline, and a level of personal independence. In some embodiments of the computer executable program, the fourth data is derived from at least one of: flexibility, a coping capacity, an ability to adapt, and a degree of personal integration. In some embodiments of the computer executable program, at least one of the activity module, the social module, the persistence module, and the stress module comprises computer executable software instructions.

BRIEF DESCRIPTION OF THE DRAWINGS

Having thus summarized the general nature of the disclosure and some of its features and advantages, certain preferred embodiments and modifications thereof will become apparent to those skilled in the art from the detailed description herein having reference to the figures that follow, of which:

FIG. 3 illustrates an example psychiatric disability determination report.

DETAILED DESCRIPTION OF THE PREFERRED EMBODIMENTS

Certain embodiments provide a reliable and valid instrument to assess mental and emotional functioning as it impacts the individual's ability to perform work-related activities. The competencies measured include an individual's awareness of self in relation to time, place and person ("orientation"), memory, cognition, the conscious subjective aspect of feeling or emotion ("affect"), and motivation.

Each of the competencies is broken down into several aspects of functioning. Basic orientation may include standard demographic data, problem solving for access to transportation, and management of finances and time. Memory functioning may include testing the recollection of patterns and symbols, recollection of instructions, physical and spatial memory, and covers auditory and visual areas. Working memory is included to assess simple levels of multi-tasking capacities. Concentration and attention span are also assessed in this category as necessary for focused and sustained performance on a task.

Cognition competency may include an assessment of an individual's conceptual level. An individual's conceptual level may range from concrete operations through the beginnings of formal operations of logic to solve problems, make judgments, avoid hazards to self and others, perform basic mathematical operations, maintain a schedule, and draw conclusions based on deductive processes.

Affect may be addressed in areas covering frustration management and response to stress, impulsivity, and response to depression and anxiety, both endogenous and exogenous. Affect may also cover capacity for empathy and feelings of self-efficacy (which is subsumed in the category of motivation issues as well). Both affect and motivation need to be considered in the vital area of ability to persist, take initiative, and complete tasks. The ability to interact with co-workers, respond appropriately to authority figures in taking directions, and make changes in routine are part of such personality competencies that may be assessed. Neuroticism, extraversion, openness to experience, agreeableness and conscientiousness, also known as the "Big Five," are also assessed.

All competency areas are measured at a minimal to moderate level to cover the lower functioning individual's ability ranges. The individual's ability may range from the mildly mentally challenged with good adaptive abilities to the borderline to low average functional range with little or no adaptive abilities.

Figure 1:
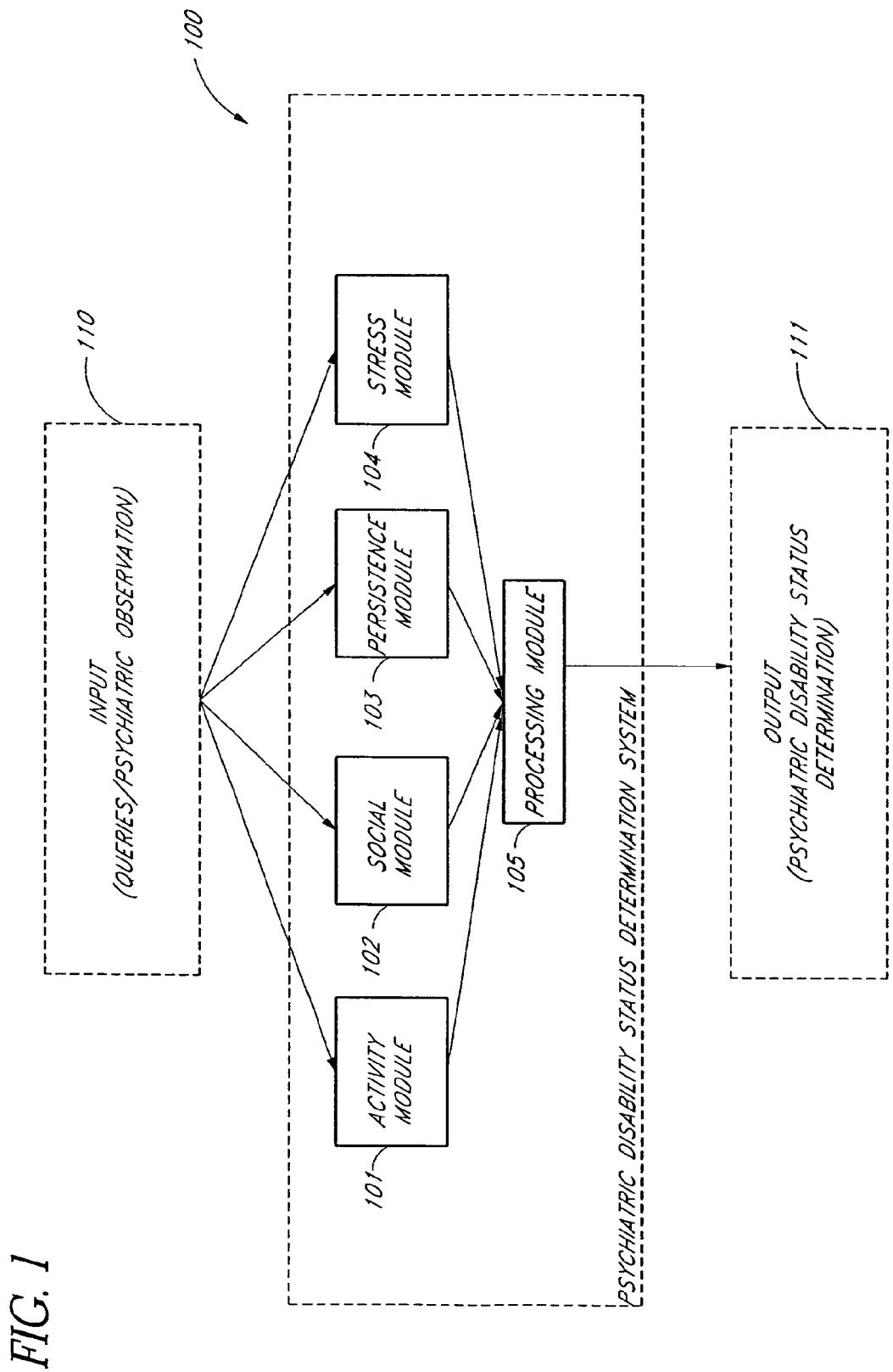
FIG. 1 illustrates one embodiment of a system for determining a psychiatric status of a person.

FIG. 1 illustrates a system for determining a psychiatric status of a person 100. In the embodiment illustrated, the system 100 comprises an activity module 101 that outputs first data indicative of the person's activities of daily living, a social module 102 that outputs second data indicative of the person's social functioning in a work like setting, a persistence module 103 that outputs third data indicative of the person's concentration persistence, a stress module 104 that outputs fourth data indicative of the person's ability to tolerate stress, and a processing module 105 that outputs fifth data 111 indicative of a psychiatric disability determination based on outputs from said activity module 101, said social module 102, said persistence module 103, and said stress module 104. The system may use input 110 from queries related to psychiatric examination or from psychiatric observation. Although five modules are shown in this embodiment, other embodiments may include additional modules which assist in determining the psychiatric status of a person.

In certain embodiments, the first data output by the activity module 101 is derived from at least one of the follow kinds of input: a level of self care, a level of personal hygiene, communication ability, travel ability, and amount of public transportation use. Other activities of daily living may also be considered. In a preferred embodiment, responses to these activities, which may include actions by the person, should reflect persistent actions taken by that person and not an occasional aberration from a habit. These inputs also preferably relate to activities which affect a work place. For example, for the personal hygiene input, if the individual is not able to maintain at least average hygiene, he will probably not be hired for work or accepted by his peers.

In certain embodiments, the second data output by the social module 102 relates to social functioning. The data is derived from social functioning as it applies to a work setting and may include an individual's capacity to at least minimally communicate, empathize and cooperate with others, interact in an accepting manner with figures of authority, and rely upon peer support. For example, some autistic individuals with impaired empathy for others may nonetheless learn the basic rules of consideration for others and appreciation of defined roles such as those between employer and employee. On the other hand, if an individual cannot appreciate the defined role differences between employer and employee, then they may have a difficult time succeeding in a work-like environment. Other activities related to social functioning other than the ones listed above may also be considered.

In certain embodiments, the third data output by the persistence module 103 is derived from at least one of the following kinds of input: the ability to remember multi-part instructions, level of persistence at a single task, level of motivation, level of self-discipline, and level of personal independence. The persistence module may also comprise a pace from a first task to a second task. Concentration, persistence, cadence, and other areas that define an individual's ability to remember and carry out single and multi-step instructions are necessary to the learning and implementation of any task. Consequently, these areas are important functions for a work setting. Other persistence related activities may also be considered. For example, if an individual has difficulty remembering multi-part instructions assigned as a function of that individual's job, then that individual will probably not succeed in his job. In addition, these persistence areas are easily measured at least in their concrete aspects. Implementing and persisting at a task also touches on the more difficult questions of motivation, self-discipline and personal independence.

In certain embodiments, the fourth data output by the stress module 104 is derived from at least one of the following kinds of input: flexibility, coping capacity, ability to adapt, and degree of personal integration. The ability to tolerate stress is also fundamental to the ability to function in a work-like environment. The concept of adaptation applies to this, as only individuals with sufficient personality flexibility can sustain gainful activity in the face of circumstances overwhelming the individual's coping capacities. The skills to shift focus to new solutions, draw upon peer support, communicate needs to administrative levels, and utilize those other factors already mentioned, necessitate a degree of personal integration that embodiments measure. Other activities related to the ability to tolerate stress other than the ones listed above may also be considered.

Each module 101, 102, 103, 104 and 105 may include one or more sub-modules. For example, a "memory" sub-module for the stress module 104 can include data about the ability of the individual to remember instructions. Modules may share common sub-modules. For example, the "memory" sub-module may be shared by multiple modules because memory information may be needed for the analysis of different components of a psychiatric disability status determination.

Figure 2:
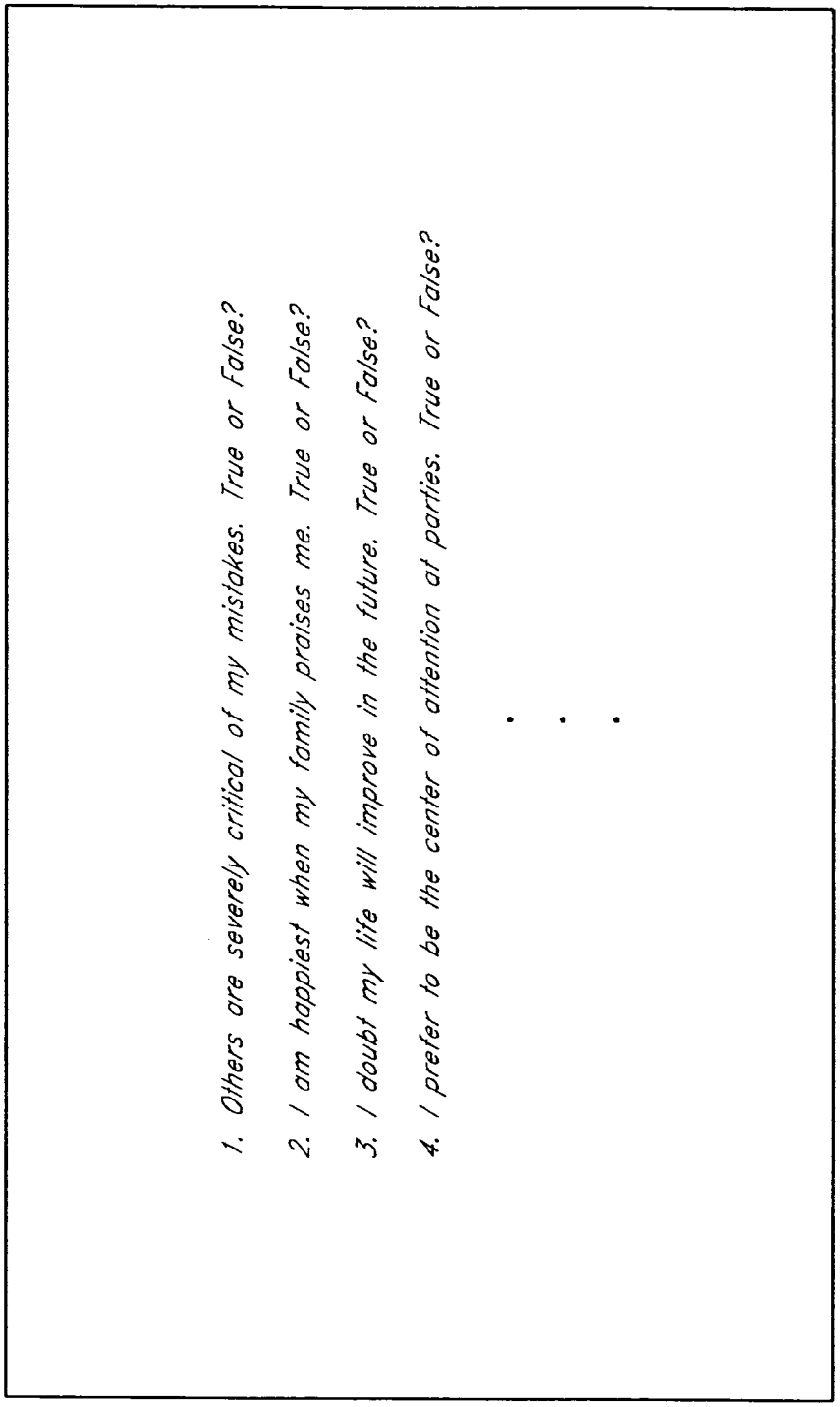
FIG. 2 is a list of sample queries presented to a person whose psychiatric status is to be determined by certain embodiments of the system.

In a preferred embodiment, the input 110 to the system modules may consist of receiving a response to one or more queries presented to the person, as illustrated in FIG. 2. In a preferred embodiment, the queries are developed specifically for the system in order to properly and accurately obtain the data each system module requires to determine the psychiatric disability status of a person. The queries may be developed with reference to psychiatric texts, mental status exams ("MSE"), or with the input of qualified healthcare professionals such as psychiatrists. Some well known MSEs include the Minnesota Multiphasic Personality Inventory test, Draw-a-Person test ("DAP"), and Rorschach test. A well known text that may be used in creating queries is the *Diagnostic and Statistical Manual of Mental Disorders, Fourth Edition* ("DSM-IV").

In certain embodiments, every query that may be required by the system for making a disability determination is identified by a field identification number (FID). Examples of FID data fields include a "patient name" field, a "blood pressure" field, a "concentration exam score" field, and so forth. Each general psychiatric evidence query is identified by a FID. A general psychiatric evidence query corresponds to a psychiatric evidence requirement specified by the system. In certain embodiments, a claimant-specific psychiatric evidence query may be generated from the general psychiatric evidence queries and based on the claimant's alleged or actual psychiatric conditions.

In one embodiment, each FID includes a category code, a rating code and a data query code, separated by the underline symbol "_". For example, a FID can take the form of "H047_SM500_T001". The category code "H047" identifies the FID to a category of queries concerning social functioning. The rating code "SM500" identifies the FID to a particular query for reliance upon peer support. The data query code "T001" identifies the FID to the data query "Do you like to be the center of attention at parties?." A query text table stores the data query codes and the query text for each of the data query codes. The table may also store a long instruction text for each data query code as an instruction or explanation. The stored query text and long instruction text can be later displayed in a provider's exam protocol, history or interview protocol, claimant questionnaire, clerk's data collection protocol, psychiatric report or rating report.

A FID can take other forms. For example, in a relational database arrangement, a rating code table can store the rating code for each data query code, and a category code table can store the category code for each data query code. Therefore a FID need only include a data query code, and the rating code and category code for the FID can be identified by referencing the rating code table and the category code table. In an object-oriented arrangement, a FID can be an object that includes a data query object field, a rating code object field and a category code object field.

An FID mapping component may organize the rules collection into a plurality of FIDs. For example, for a rating code that identifies reliance upon peer support in an MSE, the component creates a plurality of FIDs, with each FID identifying a unit of psychiatric evidence required for making a rating decision on the patient's reliance upon peer support.

The queries used for input 110 into the system modules may be presented to the person in many different ways, including orally, in writing, or in an electronic form. The queries may be presented orally to the person by any number of individuals, including but not limited to a physician, a physician's assistant, a nurse, a secretary, or other health care professionals. In a preferred embodiment, the person whose psychiatric disability status is being determined is presented with a written questionnaire, such as one shown in FIG. 2, on which he must record his responses. In other embodiments, an individual such as a healthcare professional may ask the person questions directly. The person may respond to queries in many different ways, including orally, in writing, and in an electronic form. The input 110 may additionally consist of psychiatric observations. In a preferred embodiment, the psychiatric observations are made by a qualified health care professional, such as a psychiatrist. The medical evidence collected in response to the queries is then stored into the system.

In certain embodiments, the input 110 from the individual may consist of numerical scores received in response to one or more tests of the person whose psychiatric status is being determined, such as for the MMPI. In certain embodiments, the input 110 may consist of scales or reports which are provided by other tests.

Each of the activity, social, persistence and stress module inputs may be received in whole or in part; consequently, a portion of the input data 110 may be used in order to determine the data output by the module. In certain embodiments, the input 110 may be received by a user, such as a healthcare professional who evaluates the individual's responses to the query and makes a psychiatric disability status determination based on that individual's responses. In other embodiments, an electronic system such as a computer may receive the individual's responses and provide a similar determination, albeit in electronic form.

In certain embodiments, the activity module 101, the social module 102, the persistence module 103 and the stress module 104 comprise computer executable software instructions. In other embodiments, the modules may be a combination of hardware and software, an algorithm or steps therein, or any other process. In certain embodiments, modules may run in parallel. In certain embodiments, modules may run in sequence or in series. The system 100 may be implemented within executable software that runs on one or more general purpose computers. It may, for example, run on general purpose computers that are interconnected on a local area network. Certain embodiments may be embodied within a web site, an online database network, or any other type of multi-user system that supports interactive entry of query responses. The system may also comprise a user interface configured to collect medical evidence and/or display the psychiatric disability determination. The user interface may be accessible via computers and/or other types of devices (PDAs, mobile telephones, etc.).

Referring back to FIG. 1, after medical evidence is collected from the queries (and potentially psychiatric observation) as input 110 and submitted to the activity module 101, social module 102, persistence module 103, and stress module 104, the output of those modules is then used by the processing module 105 to create a psychiatric disability determination. In certain embodiments, intervening processing or other steps may occur before the data is used by the processing module 105 to create a psychiatric disability determination 111.

FIG. 3 illustrates an example psychiatric disability determination report. In addition to information identifying the patient 301, the report includes the estimated percentages of the patient's psychiatric disability as it relates to each area of determination. For example, the patient is estimated be 80% capable of performing activities of daily living 302. The report also includes an overall determination 303 of the patient's psychiatric disability status, which in this case states that the patient would only be 35% competent in comparison to others in the job market. Furthermore, the patient is recommended not to return to his old job.

In certain embodiments, the psychiatric disability determination comprises an employment determination. The employment determination may either be whether a person can competently return to their previous job or whether a person can competently enter the job market. In some embodiments, the employment determination may be a twofold (e.g., "yes" or "no") output (ex. yes, a person can return to his old job). In other embodiments, the employment determination may be a percentage likelihood output (ex. a person can enter the job market at 55% competency compared to the rest of the market). In yet further embodiments, the employment determination may include both a twofold output and a percentage output. In a preferred embodiment, a twofold output is used to determine whether or not a person can return to their previous job, and a percentage output is used to assess how competent a person may be should they choose to enter the job market.

The psychiatric disability determination report can be used by disability claim benefit centers to determine compensation for an individual related to his mental disability. Depending on the insurance or disability program, reports of different formats can be generated to conform to the commonly accepted format of the particular program. For example, the medical evidence queries can be grouped by difficulty of understanding on a report for a first insurance program, and grouped by module on another report for a second disability program.

The psychiatric disability determination report may be output to an output device. The report may be output as a data set, which includes data relevant to the disability determination report. Outputting or publication of the report may include, but is not limited to, printing, writing, displaying, storing, transmitting, electronically sending, or manually sending the report at any time after the report is generated. Output devices may include but are not limited to, a display monitor, a printer, paper, the human voice, computer memory, volatile (such as RAM) or non-volatile (such as a hard disk drive), or an electronically generated voice.

From the foregoing description, it will be appreciated that a novel approach has been disclosed for the determination of the psychiatric disability status of a person. While the components, techniques and aspects of the disclosure have been described with a certain degree of particularity, it is manifest that many changes may be made in the specific designs, constructions and methodology herein above described without departing from the spirit and scope of this disclosure.

Various modifications and applications of the disclosure may occur to those who are skilled in the art, without departing from the true spirit or scope of the disclosure. It should be understood that the disclosure is not limited to the embodiments set forth herein for purposes of exemplification, but is to be defined only by a fair reading of the appended claims, including the full range of equivalency to which each element thereof is entitled.

What is claimed is:

1. A system for determining, using a computer, a psychiatric status of a person, the system comprising:
   a non-transitory computer-readable medium programmed to output, by a computer, data indicative of a psychiatric disability determination based on first data indicative of the person's activities of daily living, second data indicative of the person's social functioning in a work-like setting, third data indicative of the person's concentration persistence, and fourth data indicative of the person's ability to tolerate stress; and
   a non-transitory computer-readable medium programmed to determine, based on the psychiatric disability determination, whether the person can perform the person's job in the person's workplace, and to provide a recommendation that the person return to his job or a recommendation that the person not return to his job;

wherein the determination whether the person can perform the person's job in the person's workplace varies based on the person's job and varies based on the person's workplace; and wherein the psychiatric disability determination comprises a degree of psychiatric disability relative to each of the first data, second data, third data, and fourth data.

2. The system of claim 1, wherein said first data is derived from at least one of: a level of self-care, a level of personal hygiene, communication ability, travel ability, and an amount of public transportation use.

3. The system of claim 1, wherein said second data is derived from at least one of: a communication capacity, an extent of cooperation with others, a level of acceptance of authority, and a reliance upon peer support.

4. The system of claim 1, wherein said third data is derived from at least one of: an ability to remember multi-part instructions, a level of persistence at a single task, a level of motivation, a level of self-discipline, and a level of personal independence.

5. The system of claim 1, wherein said fourth data is derived from at least one of: flexibility, a coping capacity, an ability to adapt, and a degree of personal integration.

6. The system of claim 1, further comprising a user interface configured to display the psychiatric disability determination.

7. A method for determining a psychiatric status of a person, the method comprising:

receiving, by a computer, first data indicative of the person's activities of daily living;

receiving, by the computer, second data indicative of the person's social functioning in a work-like setting;

receiving, by the computer, third data indicative of the person's concentration persistence;

receiving, by the computer, and fourth data indicative of the person's ability to tolerate stress;

processing, by the computer, said first, second, third and fourth data so as to generate a psychiatric disability determination; and determining, based on the psychiatric disability determination, whether the person can perform the person's job in the person's workplace; and providing a recommendation that the person return to his job or a recommendation that the person not return to his job;

wherein the determination whether the person can perform the person's job in the person's workplace varies based on the person's job and varies based on the person's workplace; and wherein the psychiatric disability determination comprises a degree of psychiatric disability relative to each of the first data, second data, third data, and fourth data.

8. The method of claim 7, wherein said psychiatric disability determination comprises an employment determination.

9. The method of claim 7, wherein said receiving the first, second, third and/or fourth data comprises receiving at least a portion of the first, second, third and/or fourth data from a user.

10. The method of claim 7, wherein said receiving the first, second, third and/or fourth data comprises receiving at least a portion of the first, second, third and/or fourth data from an electronic database.

11. The method of claim 7, wherein said receiving the first, second, third and/or fourth data comprises receiving numerical scores in response to one or more tests of the person.

12. The method of claim 7, wherein said receiving the first, second, third and/or fourth data comprises receiving response to one or more queries presented to the person.

13. The method of claim 7, wherein the concentration persistence comprises a pace from a first task to a second task.

14. A non-transitory computer-readable medium comprising instructions that perform the method comprising:

receiving, by a computer, first data indicative of the person's activities of daily living;

receiving, by the computer, second data indicative of the person's social functioning in a work-like setting;

receiving, by the computer, third data indicative of the person's concentration persistence;

receiving, by the computer, and fourth data indicative of the person's ability to tolerate stress;

processing, by the computer, said first, second, third and fourth data so as to generate a psychiatric disability determination; and determining, based on the psychiatric disability determination, whether the person can perform the person's job in the person's workplace; and providing a recommendation that the person return to his job or a recommendation that the person not return to his job;

wherein the determination whether the person can perform the person's job in the person's workplace varies based on the person's job and varies based on the person's workplace; and wherein the psychiatric disability determination comprises a degree of psychiatric disability relative to each of the first data, second data, third data, and fourth data.

15. The computer-readable medium of claim 14, wherein said psychiatric disability determination comprises an employment determination.

16. The computer-readable medium of claim 14, wherein said receiving the first, second, third and/or fourth data comprises receiving at least a portion of the first, second, third and/or fourth data from a user.

17. The computer-readable medium of claim 14, wherein said receiving the first, second, third and/or fourth data comprises receiving at least a portion of the first, second, third and/or fourth data from an electronic database.

18. The computer-readable medium of claim 14, wherein said receiving the first, second, third and/or fourth data comprises receiving numerical scores in response to one or more tests of the person.

19. The computer-readable medium of claim 14, wherein said receiving the first, second, third and/or fourth data comprises receiving response to one or more queries presented to the person.

20. The computer-readable medium of claim 14, wherein the concentration persistence comprises a pace from a first task to a second task.

21. The system of claim 1, wherein said third data is derived from an ability to remember multi-part instructions.

22. A system for determining, using a computer, a psychiatric status of a person, the system comprising:

a computer-readable medium programmed to output, by a computer, data indicative of a psychiatric disability determination based on first data indicative of the person's activities of daily living, second data indicative of the person's social functioning in a work-like setting, third data indicative of the person's concentration persistence, including an ability to remember multi-part instructions, and fourth data indicative of the person's ability to tolerate stress;

a computer-readable medium programmed to determine, based on the psychiatric disability determination, whether the person can perform the person's job in the person's workplace, and to provide a recommendation that the person return to his job or a recommendation that the person not return to his job;

wherein the determination whether the person can perform the person's job in the person's workplace varies based on the person's job and varies based on the person's workplace; and wherein the psychiatric disability determination comprises a degree of psychiatric disability relative to each of the first data, second data, third data, and fourth data.

23. The system of claim 1, wherein the psychiatric disability determination comprises a degree of competence of the person performing the person's job in the person's workplace.

\* \* \* \* \*